United States Patent
Yea et al.

(10) Patent No.: US 12,398,211 B2
(45) Date of Patent: Aug. 26, 2025

(54) GFRAL-ANTAGONISTIC ANTIBODY AND USE THEREOF

(71) Applicant: DAEGU GYEONGBUK INSTITUTE OF SCIENCE AND TECHNOLOGY, Daegu (KR)

(72) Inventors: Kyung Moo Yea, Daegu (KR); Beom Yong Lee, Daegu (KR); Jong Won Jeong, Daegu (KR)

(73) Assignee: DAEGU GYEONGBUK INSTITUTE OF SCIENCE AND TECHNOLOGY, Daegu (KR)

( * ) Notice: Subject to any disclaimer, the term of this patent is extended or adjusted under 35 U.S.C. 154(b) by 528 days.

(21) Appl. No.: 17/928,979

(22) PCT Filed: Jun. 2, 2021

(86) PCT No.: PCT/KR2021/006865
§ 371 (c)(1),
(2) Date: Dec. 1, 2022

(87) PCT Pub. No.: WO2021/246773
PCT Pub. Date: Dec. 9, 2021

(65) Prior Publication Data
US 2023/0295307 A1    Sep. 21, 2023

(30) Foreign Application Priority Data
Jun. 4, 2020 (KR) .......... 10-2020-0067543
May 28, 2021 (KR) .......... 10-2021-0068874

(51) Int. Cl.
*C07K 16/28* (2006.01)
*A61K 39/00* (2006.01)
*A61P 43/00* (2006.01)

(52) U.S. Cl.
CPC .......... *C07K 16/2863* (2013.01); *A61K 39/00* (2013.01); *A61P 43/00* (2018.01); *C07K 2317/565* (2013.01)

(58) Field of Classification Search
None
See application file for complete search history.

(56) References Cited

U.S. PATENT DOCUMENTS

| 10,174,119 B2 | 1/2019 | Shen et al. |
| 2014/0193427 A1 | 7/2014 | Lerner et al. |

FOREIGN PATENT DOCUMENTS

| JP | 2019510739 | 4/2019 |
| JP | 2019-513018 | 5/2019 |
| JP | 2019-513224 | 5/2019 |
| WO | 2013012648 | 1/2013 |

OTHER PUBLICATIONS

Samuel N. Breit et al., "Targeting Obesity and Cachexia: Identification of the GFRAL Receptor-MIC-1/GDF15 Pathway", Trends in Molecular Medicine, Dec. 2017, vol. 23, No. 12.
Paul J Emmerson et al., "The metabolic effects of GDF15 are mediated by the orphan receptor GFRAL", nature medicine vol. 23, No. 10, 1215-1219, Oct. 2017, total 9 pages.
Jer-Yuan Hsu et al., "Non-homeostatic body weight regulation through a brainstem-restricted receptor for GDF15 (Includes methods)", Nature, Jan. 1, 2017 (Jan. 1, 2017 ).
Tito Borner et al., "GDF15 Induces Anorexia through Nausea and Emesis", Cell Metabolism, Cell Press, United States, val. 31, No. 2, Jan. 9, 2020 (Jan. 9, 2020), p. 351.
Beom Yong Lee et al., "GDNF family receptor 1-12 alpha-like antagonist antibody alleviates chemotherapy-induced cachexia in melanoma-bearing mice", Journal of Cachexia, Sarcopenia and Muscle Dec. 2013, val. 14, No. 3, Jun. 5, 2023 (Jun. 5, 2023), pp. 1441-1453.

*Primary Examiner* — Ruixiang Li
(74) *Attorney, Agent, or Firm* — LEX IP MEISTER, PLLC

(57) ABSTRACT

The present invention relates to a GFRAL-antagonistic antibody and a use thereof, and more particularly, to an anti-GFRAL antibody comprising a heavy chain CDR and a light chain CDR of specific sequences, and an antigen-binding fragment thereof. The anti-GFRAL antibody is expected to be usefully utilized for ameliorating or treating anorexia-cachexia syndrome associated with cancer, and adverse effects of chemotherapeutic drugs.

4 Claims, 12 Drawing Sheets
Specification includes a Sequence Listing.

[FIG. 1]
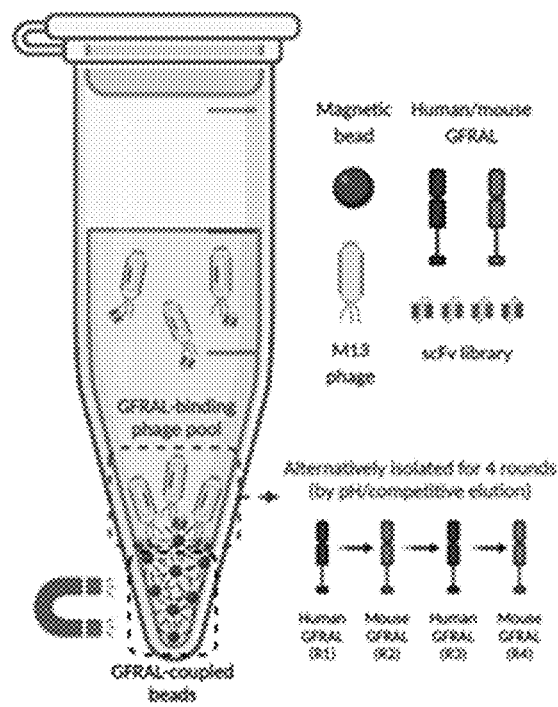
[FIG. 2]
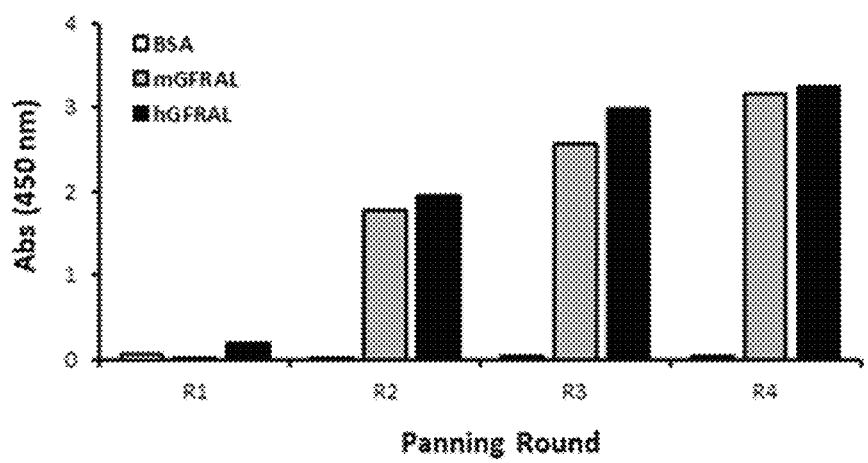

[FIG. 3]
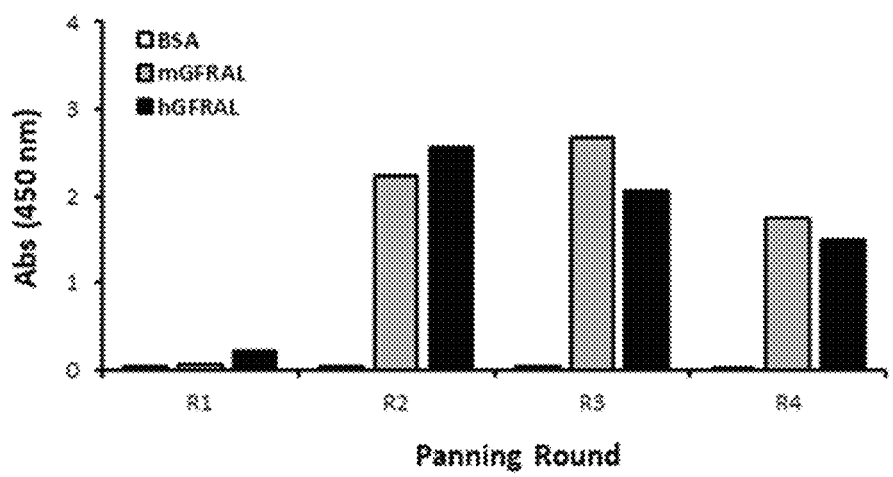
[FIG. 4]
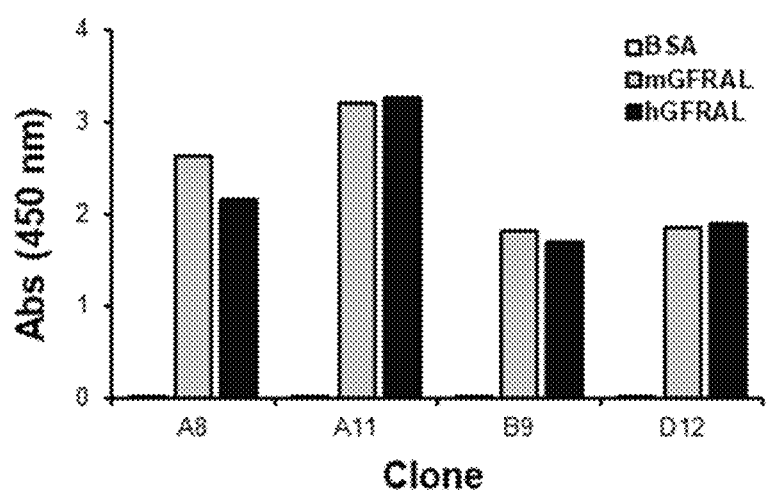

[FIG. 5]
|     | VH CDR1  | VH CDR2  | VH CDR3            |
| --- | -------- | -------- | ------------------ |
| A8  | GFTFDDYA | ISWNSGNI | CAKDISYGSGSSFDY    |
| A11 | GFTFSSYG | ISYDGSNK | CAKVTSGGDFWSGNYYYYDV |
| B9  | GGTFSSYA | IIPIFGTA | CARPSDRYSLTTPLAFDI |
| D12 | GYTFTGYY | INPNSGGT | CAKDQWLGHYGSDV     |
|     | VL CDR1   | VL CDR2 | VL CDR3    |
| --- | --------- | ------- | ---------- |
| A8  | SSDVGGYNY | GVT     | LSYAGSYNWV |
| A11 | SLRDYY    | GKN     | NSRGSSGNQWV |
| B9  | SSDVGGYDY | EVS     | SSYAGSNDLV |
| D12 | QGISSS    | AAS     | QQTYHTPQT  |
[FIG. 6]
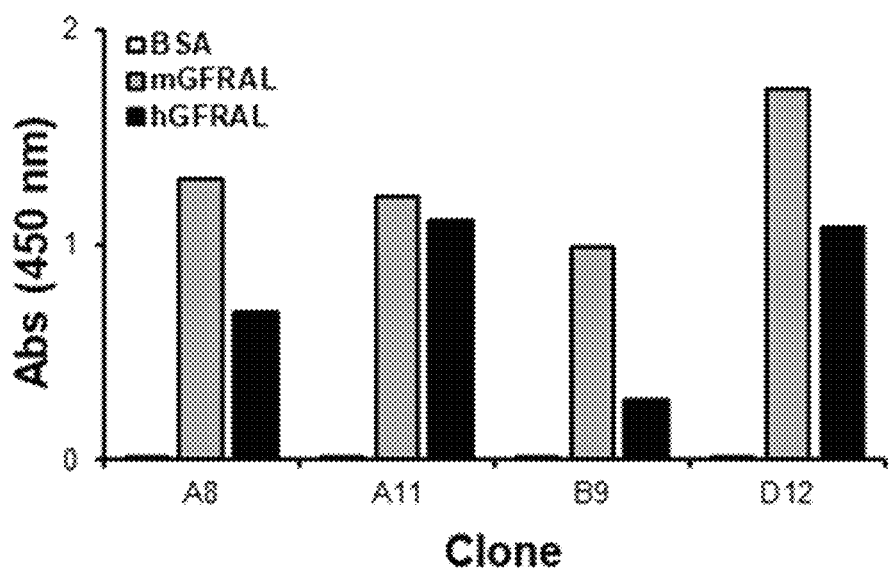

[FIG. 7]
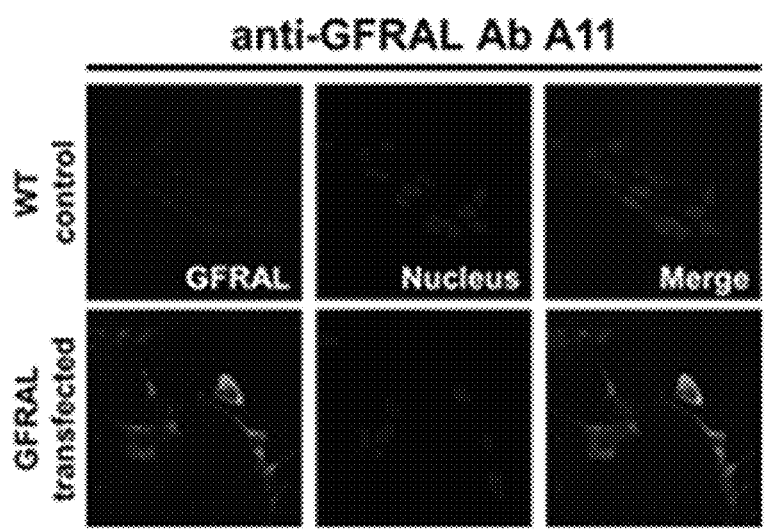
[FIG. 8]
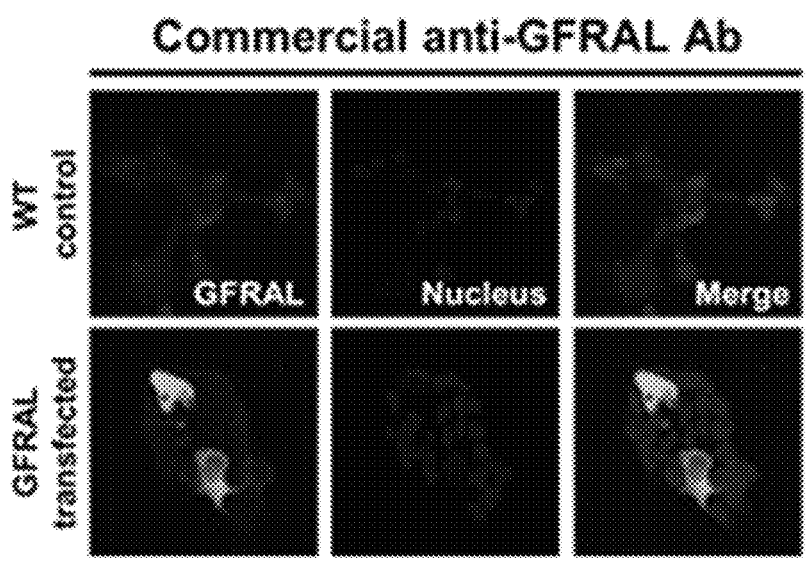

[FIG. 9]
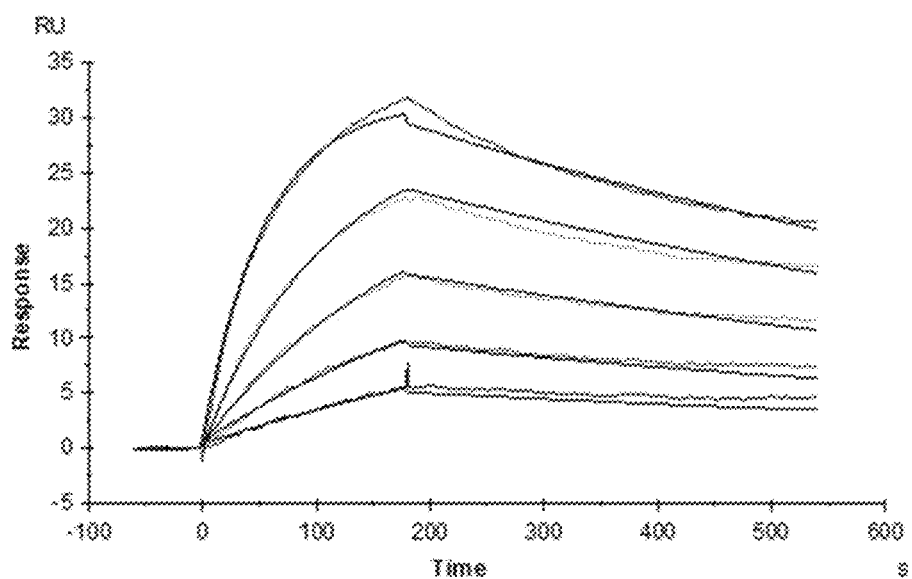
[FIG. 10]
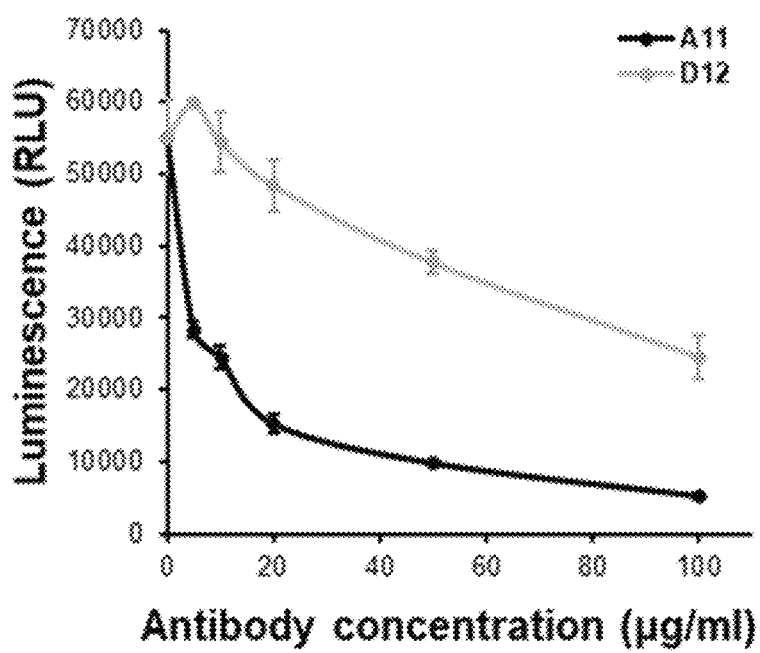

[FIG. 11]
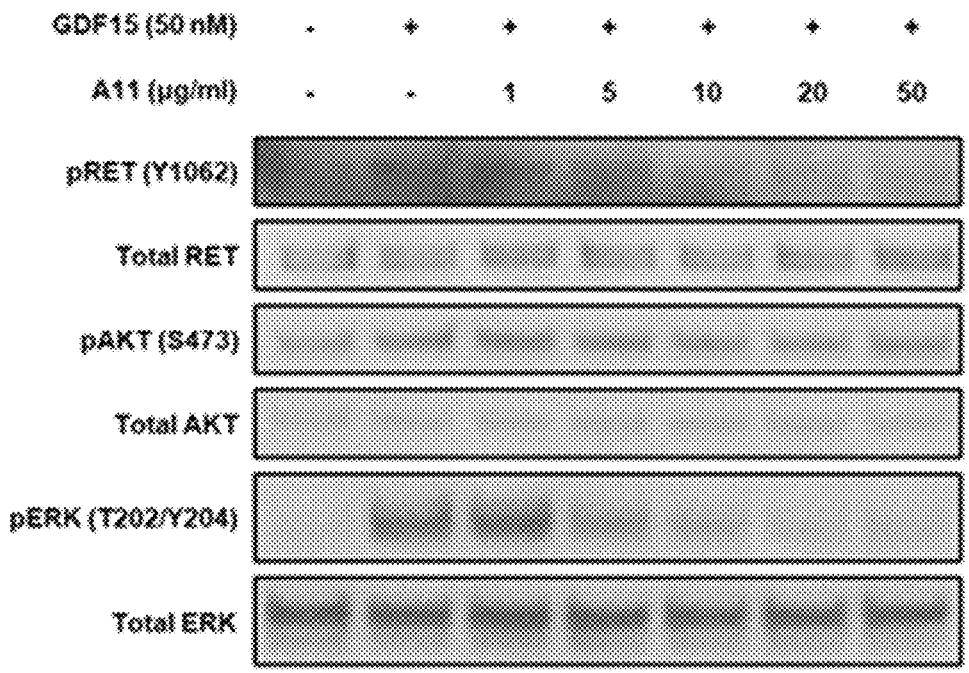
[FIG. 12]
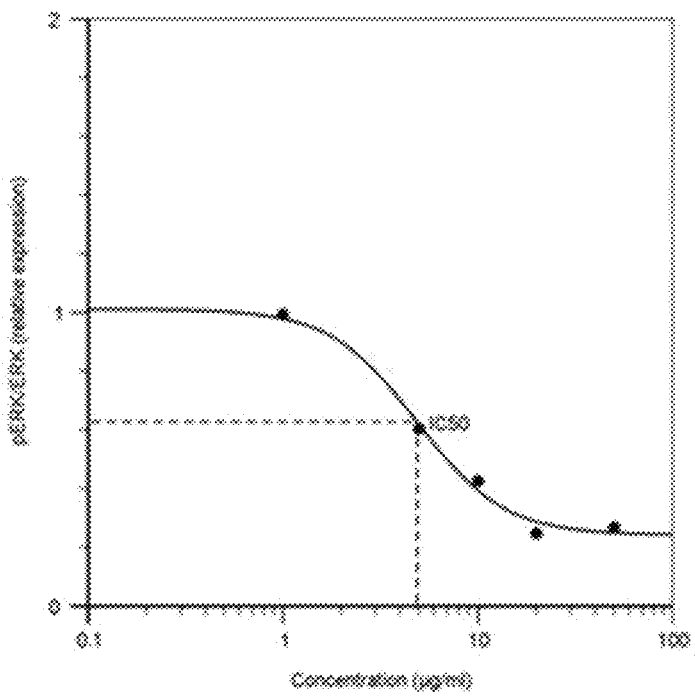

[FIG. 13]
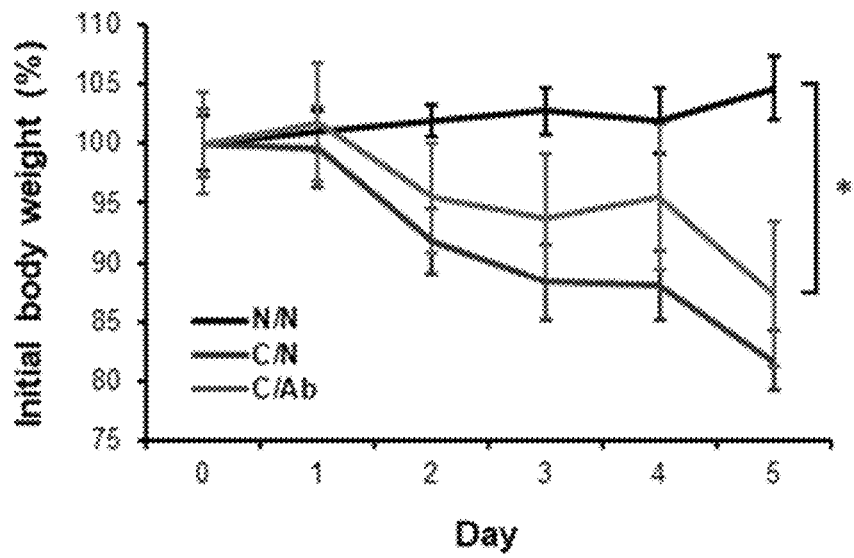
[FIG. 14]
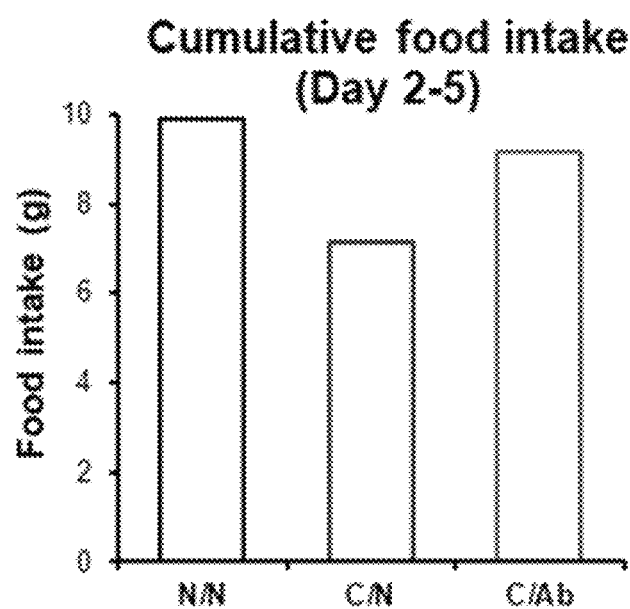

[FIG. 15]
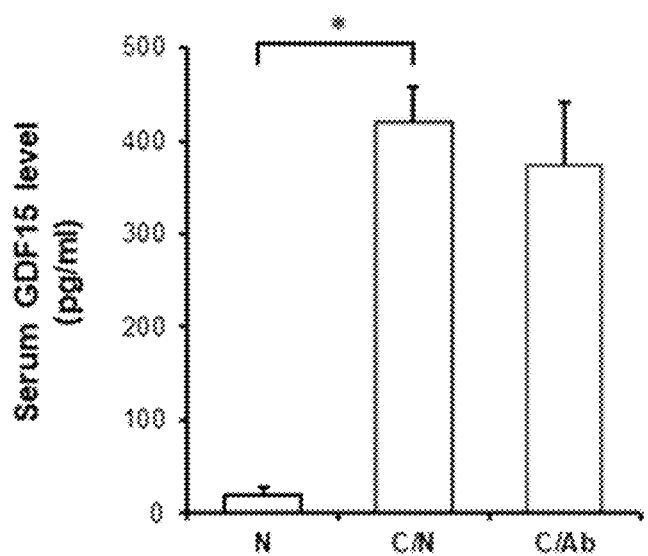
[FIG. 16]
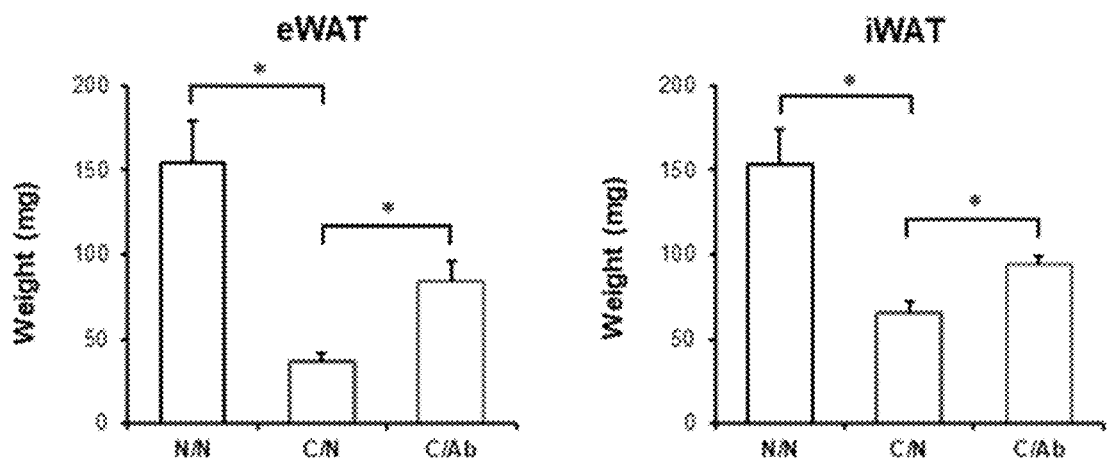

[FIG. 17]
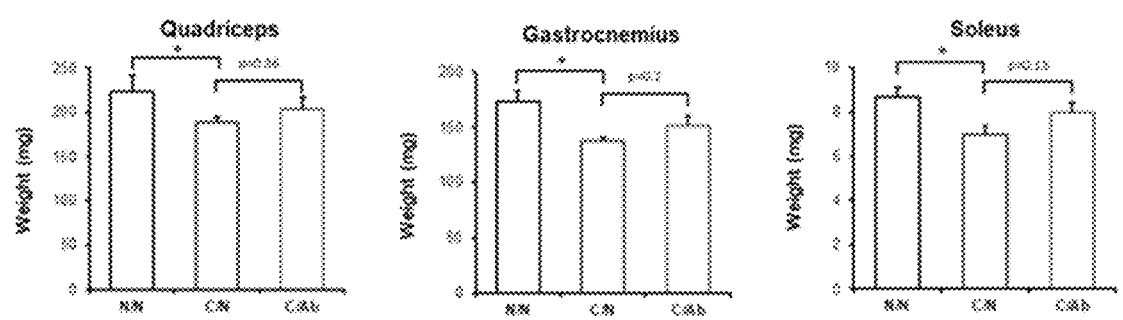
[FIG. 18]
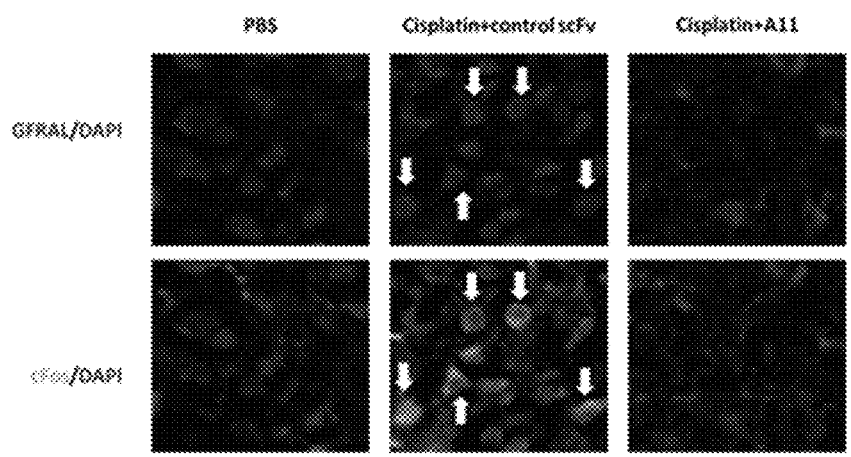

[FIG. 19]
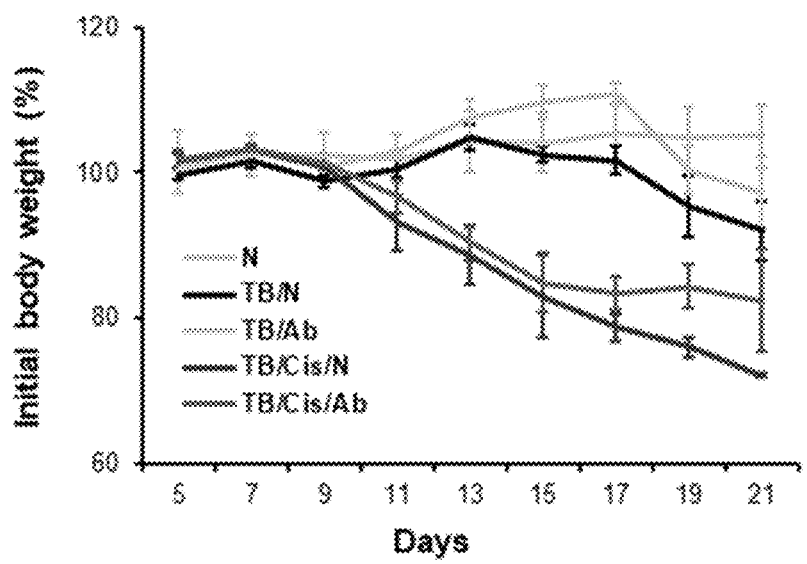
[FIG. 20]
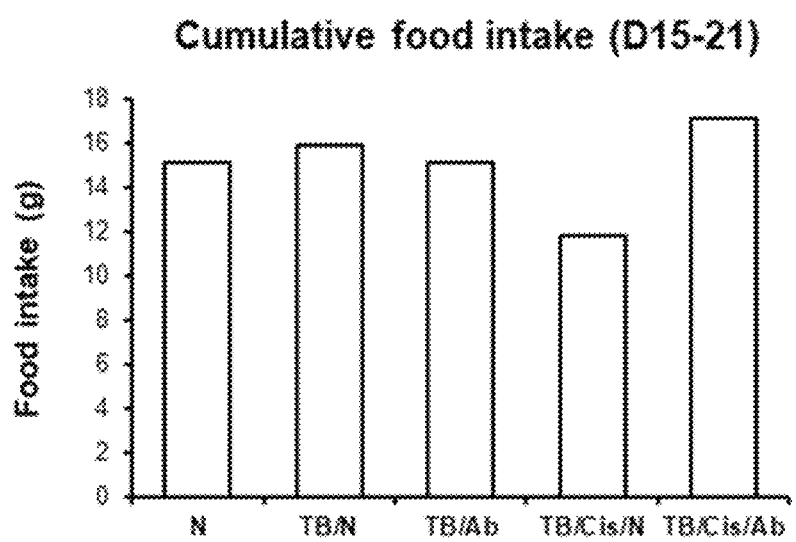

[FIG. 21]
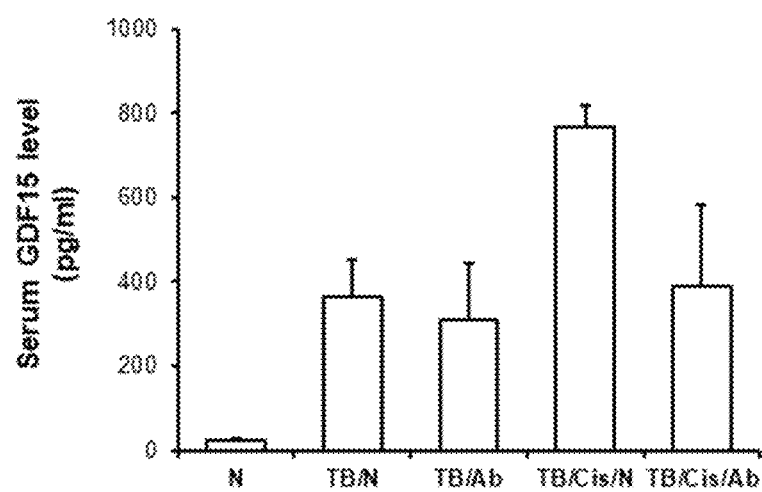
[FIG. 22]
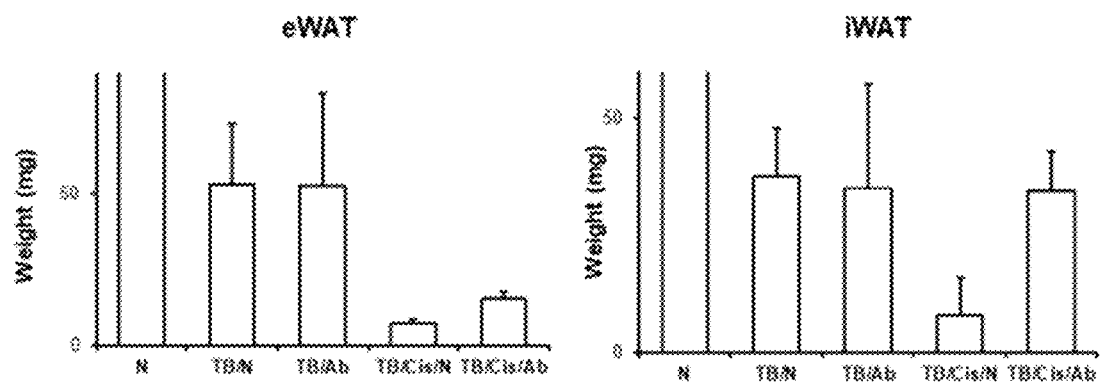

[FIG. 23]
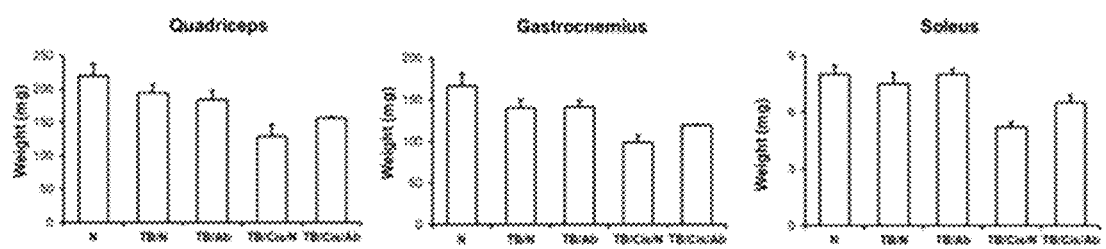

GFRAL-ANTAGONISTIC ANTIBODY AND USE THEREOF

TECHNICAL FIELD

The present disclosure relates to a GFRAL-antagonistic antibody and a use thereof.

BACKGROUND ART

Since derivation of first monoclonal antibody in 1975, antibody therapeutic agents were first released in 1994 using characteristics of antibodies exhibiting strong binding affinity against antigens, and therapeutic antibodies are recording fastest growth among pharmaceuticals. As of 2007, the global market size for therapeutic antibodies is 27 billion, showing continued growth from 44.7 billion in 2011 to 57.7 billion in 2016. Based on such growth, as of 2014, antibody drugs accounted for 10% of global drug sales, taking up 6 out of the top 10 drug sales in 2016. Compared to existing therapeutic agents which are based on chemically synthesized compounds, antibody drugs have been proven to cause relatively few side effects while ensuring excellent therapeutic efficacy owing to high binding specificity and stability in vivo. Thus, a field of development for antibody drugs is drawing attention as the next-generation core field of new drug R&D. Moreover, it seems that antibody drugs will be next-generation therapeutics due to rapid development in expression, production, purification, and engineering technology for high molecular proteins which are essential for the development of antibody drugs as well as the high success rate in clinical trials.

Cancer-related anorexia-cachexia syndrome (CACS) refers to an excessive catabolic state characterized by persistent anorexia and weight loss. CACS causes increased breakdown of muscle and fat, nutritional and metabolic imbalances, and an increase in basal metabolic rate, leading to deterioration in overall body functions. Such CACS is one of the major causes of death among cancer patients and is also the most important independent prognostic factor to predict negative treatment outcome. Furthermore, accompanied by restriction in nutrient intake due to treatment such as chemotherapy, radiation therapy, or surgery, response rate to treatment is low, and effective treatment becomes hard to proceed, which is a main cause of deteriorating survival rate or quality of life of patients. Nevertheless, CACS is underestimated, and unmet medical needs still remain. Currently, general appetite stimulants and muscle synthesis stimulants seem to hardly bring effective treatment outcome.

Growth differentiation factor 15 (GDF15) is a cytokine that plays various roles in vivo by involving in immune responses and metabolism. Under normal circumstances, GDF15 is expressed at low concentrations in most tissues, and level thereof is greatly increased when tissues such as liver, kidney, heart, and lung are damaged. In 2007, it was found that GDF15 is a substance that induces cachexia by anorexia in the body of prostate cancer patients, and there is a clear correlation between weight loss through anorexia in cancer patients and GDF15 concentration, with the concentration of GDF15 in the blood of prostate cancer patients increased 10-100 times that of normal people (Nature medicine 2007; 12(10); 1333-40). In 2016, it was disclosed that GDF15 is a major cytokine that induces cachexia in various carcinomas, and GDF15 antibody showed cachexia alleviating effect by increasing weight and reducing loss of muscle and adipose tissues in various cancer cachexia mouse models (Journal of cachexia, sarcopenia and muscle 2016; 7: 467-482).

It was reported in 2015 that treatment of chemotherapy such as cisplatin caused side effects such as increased expression of GDF15 and increased resistance to chemotherapy through anorexia and cachexia (PLoS One 2015; 10(1); e0115372). In 2017, it was found that GDF15 suppresses appetite through receptor GFRAL, and that signal transduction of GDF15 acts in a GFRAL-dependent manner after treatment of GDF15 alone or treatment of cisplatin (Nature 2017; 550(7675); 255-259). GFRAL transmits a signal to the inside of cells with RET, a co-receptor, and is specifically expressed in the hindbrain area postrema (AP) and nucleus tractus solitaris (NTS) regions outside the blood-brain barrier where antibody drugs are accessible.

Accordingly, anti-GFRAL antibody alleviates anorexia of cancer patients suffering from CACS due to administration of platinum anticancer drugs such as cisplatin, and reduces resistance to chemotherapy through weight gain and an increase in skeletal muscle metabolism, thereby contributing to enhancement of welfare and life extension of cancer patients.

DISCLOSURE

Technical Goals

An object of the present disclosure is to provide an anti-GFRAL antibody or antigen-binding fragment thereof.

Another object of the present disclosure is to provide a nucleic acid molecule encoding the anti-GFRAL antibody or antigen-binding fragment thereof, a recombinant expression vector including the nucleic acid molecule, and a cell transformed with the recombinant expression vector.

Another object of the present disclosure is to provide a composition for preventing, alleviating, or treating cancer-related anorexia-cachexia syndrome (CACS), including the anti-GFRAL antibody or antigen-binding fragment thereof as an active ingredient.

Another object of the present disclosure is to provide a composition for preventing, alleviating, or treating anorexia or cachexia caused by an anticancer agent, including the anti-GFRAL antibody or antigen-binding fragment thereof as an active ingredient.

Technical Solutions

To achieve the above object, example embodiments of the present disclosure provide an anti-GFRAL antibody or antigen-binding fragment thereof, including a heavy chain variable region including a heavy chain CDR1 having an amino acid sequence represented by SEQ ID NO: 1, a heavy chain CDR2 having an amino acid sequence represented by SEQ ID NO: 2, and a heavy chain CDR3 having an amino acid sequence represented by SEQ ID NO: 3; and a light chain variable region including a light chain CDR1 having an amino acid sequence represented by SEQ ID NO: 4, a light chain CDR2 having an amino acid sequence represented by SEQ ID NO: 5, and a light chain CDR3 having an amino acid sequence represented by SEQ ID NO: 6.

In addition, example embodiments of the present disclosure provide an anti-GFRAL antibody or antigen-binding fragment thereof, including a heavy chain variable region including a heavy chain CDR1 having an amino acid sequence represented by SEQ ID NO: 7, a heavy chain CDR2 having an amino acid sequence represented by SEQ ID NO: 8, and a heavy chain CDR3 having an amino acid sequence represented by SEQ ID NO: 9; and a light chain variable region including a light chain CDR1 having an amino acid sequence represented by SEQ ID NO: 10, a light chain CDR2 having an amino acid sequence represented by SEQ ID NO: 11, and a light chain CDR3 having an amino acid sequence represented by SEQ ID NO: 12.

In addition, example embodiments of the present disclosure provide an anti-GFRAL antibody or antigen-binding fragment thereof, including a heavy chain variable region including a heavy chain CDR1 having an amino acid sequence represented by SEQ ID NO: 13, a heavy chain CDR2 having an amino acid sequence represented by SEQ ID NO: 14, and a heavy chain CDR3 having an amino acid sequence represented by SEQ ID NO: 15; and a light chain variable region including a light chain CDR1 having an amino acid sequence represented by SEQ ID NO: 16, a light chain CDR2 having an amino acid sequence represented by SEQ ID NO: 17, and a light chain CDR3 having an amino acid sequence represented by SEQ ID NO: 18.

In addition, example embodiments of the present disclosure provide an anti-GFRAL antibody or antigen-binding fragment thereof, including a heavy chain variable region including a heavy chain CDR1 having an amino acid sequence represented by SEQ ID NO: 19, a heavy chain CDR2 having an amino acid sequence represented by SEQ ID NO: 20, and a heavy chain CDR3 having an amino acid sequence represented by SEQ ID NO: 21; and a light chain variable region including a light chain CDR1 having an amino acid sequence represented by SEQ ID NO: 22, a light chain CDR2 having an amino acid sequence represented by SEQ ID NO: 23, and a light chain CDR3 having an amino acid sequence represented by SEQ ID NO: 24.

In addition, example embodiments of the present disclosure provide a nucleic acid molecule encoding the anti-GFRAL antibody or antigen-binding fragment thereof.

In addition, example embodiments of the present disclosure provide a recombinant expression vector including the nucleic acid molecule.

In addition, example embodiments of the present disclosure provide a cell transformed with the recombinant expression vector.

In addition, example embodiments of the present disclosure provide a pharmaceutical composition for preventing or treating cancer-related anorexia-cachexia syndrome (CACS), including the anti-GFRAL antibody or antigen-binding fragment thereof as an active ingredient.

In addition, example embodiments of the present disclosure provide a health functional food composition for preventing or alleviating cancer-related anorexia-cachexia syndrome (CACS), including the anti-GFRAL antibody or antigen-binding fragment thereof as an active ingredient.

In addition, example embodiments of the present disclosure provide a pharmaceutical composition for preventing or treating anorexia or cachexia caused by an anticancer agent, including the anti-GFRAL antibody or antigen-binding fragment thereof as an active ingredient.

In addition, example embodiments of the present disclosure provide a health functional food composition for preventing or alleviating anorexia or cachexia caused by an anticancer agent, including the anti-GFRAL antibody or antigen-binding fragment thereof as an active ingredient.

Advantageous Effects

Example embodiments of the present disclosure relates to a GFRAL-antagonistic antibody and a use thereof, and more particularly, to an anti-GFRAL antibody or antigen-binding fragment thereof, including a heavy chain CDR and a light chain CDR of specific sequences. The anti-GFRAL antibody is expected to be useful for alleviating or treating cancer-related anorexia-cachexia syndrome and side effects of chemotherapeutic anticancer drugs.

BRIEF DESCRIPTIONS OF THE DRAWINGS

FIG. 1 shows a phage display method using epoxy beads and antigen GFRAL (mouse and human).

FIG. 2 shows a result identifying a binding ability to GFRAL of bacteriophage library for each round of phage display after elution using an acidic buffer through a polyphage enzyme-linked immunosorbent assay.

FIG. 3 shows a result identifying the binding ability to GFRAL of bacteriophage library for each round of phage display after elution using a ligand GDF15 through a polyphage enzyme-linked immunosorbent assay.

FIG. 4 shows a result identifying the binding ability to GFRAL of four monoclones after performing a monophagy enzyme-linked immunosorbent assay.

FIG. 5 shows a result identifying an amino acid sequence of each CDR region of four monoclones.

FIG. 6 shows a result identifying the binding ability to GFRAL through an enzyme-linked immunosorbent assay after expression and purification of four monoclones into proteins.

FIG. 7 shows a result identifying binding of monoclone A11 to GFRAL through immunocytochemistry.

FIG. 8 shows a result identifying binding of commercial antibody to GFRAL through immunocytochemistry.

FIG. 9 shows a result identifying the binding ability of monoclone A11 to GFRAL through surface plasmon resonance.

FIG. 10 shows a result identifying a decrease in luciferase expression by monoclone A11 in GFRAL/RET/luciferase overexpressing cells through a reporter assay.

FIG. 11 shows a result identifying a decrease in pERK expression by monoclone A11 in GFRAL/RET overexpressing cells through Western blot.

FIG. 12 shows a result of FIG. 11 numerically expressed by densitometry.

FIG. 13 shows a result identifying alleviation of the weight reduction effect of cisplatin by monoclone A11 in a mouse model.

FIG. 14 shows a result identifying alleviation of the appetite reduction effect of cisplatin by monoclone A11 in a mouse model.

FIG. 15 shows a result identifying the concentration of GDF15 changed by cisplatin in a mouse model.

FIG. 16 shows results identifying alleviation of the fat mass reduction effect of cisplatin by monoclone A11 in a mouse model.

FIG. 17 shows results identifying alleviation of the muscle mass reduction effect of cisplatin by monoclone A11 in a mouse model.

FIG. 18 shows results identifying inhibition of cisplatin activity by monoclone A11 in a mouse model through immunohistochemistry.

FIG. 19 shows a result identifying alleviation of the weight reduction effect of cisplatin by monoclone A11 in an allograft mouse tumor model.

FIG. 20 shows a result identifying alleviation of the appetite reduction effect of cisplatin by monoclone A11 in an allograft mouse tumor model.

FIG. 21 shows a result identifying concentration of GDF15 changed by cisplatin in an allograft mouse tumor model.

FIG. 22 shows results identifying alleviation of the fat mass reduction effect of cisplatin by monoclone A11 in an allograft mouse tumor model.

FIG. 23 shows results identifying alleviation of the muscle mass reduction effect of cisplatin by monoclone A11 in an allograft mouse tumor model.

BEST MODE

An example embodiment of the present disclosure provides an anti-GFRAL antibody or antigen-binding fragment thereof, including a heavy chain variable region including a heavy chain CDR1 having an amino acid sequence represented by SEQ ID NO: 1, a heavy chain CDR2 having an amino acid sequence represented by SEQ ID NO: 2, and a heavy chain CDR3 having an amino acid sequence represented by SEQ ID NO: 3; and a light chain variable region including a light chain CDR1 having an amino acid sequence represented by SEQ ID NO: 4, a light chain CDR2 having an amino acid sequence represented by SEQ ID NO: 5, and a light chain CDR3 having an amino acid sequence represented by SEQ ID NO: 6.

In addition, an example embodiment of the present disclosure provides an anti-GFRAL antibody or antigen-binding fragment thereof, including a heavy chain variable region including a heavy chain CDR1 having an amino acid sequence represented by SEQ ID NO: 7, a heavy chain CDR2 having an amino acid sequence represented by SEQ ID NO: 8, and a heavy chain CDR3 having an amino acid sequence represented by SEQ ID NO: 9; and a light chain variable region including a light chain CDR1 having an amino acid sequence represented by SEQ ID NO: 10, a light chain CDR2 having an amino acid sequence represented by SEQ ID NO: 11, and a light chain CDR3 having an amino acid sequence represented by SEQ ID NO: 12.

In addition, an example embodiment of the present disclosure provides an anti-GFRAL antibody or antigen-binding fragment thereof, including a heavy chain variable region including a heavy chain CDR1 having an amino acid sequence represented by SEQ ID NO: 13, a heavy chain CDR2 having an amino acid sequence represented by SEQ ID NO: 14, and a heavy chain CDR3 having an amino acid sequence represented by SEQ ID NO: 15; and a light chain variable region including a light chain CDR1 having an amino acid sequence represented by SEQ ID NO: 16, a light chain CDR2 having an amino acid sequence represented by SEQ ID NO: 17, and a light chain CDR3 having an amino acid sequence represented by SEQ ID NO: 18.

In addition, an example embodiment of the present disclosure provides an anti-GFRAL antibody or antigen-binding fragment thereof, including a heavy chain variable region including a heavy chain CDR1 having an amino acid sequence represented by SEQ ID NO: 19, a heavy chain CDR2 having an amino acid sequence represented by SEQ ID NO: 20, and a heavy chain CDR3 having an amino acid sequence represented by SEQ ID NO: 21; and a light chain variable region including a light chain CDR1 having an amino acid sequence represented by SEQ ID NO: 22, a light chain CDR2 having an amino acid sequence represented by SEQ ID NO: 23, and a light chain CDR3 having an amino acid sequence represented by SEQ ID NO: 24.

Here, CDRs having amino acids represented by SEQ ID NO: 1 to SEQ ID NO: 24 are shown in Table 1.

TABLE 1

| | VH | | | VL | | |
|---|---|---|---|---|---|---|
| | CDR1 | CDR2 | CDR3 | CDR1 | CDR2 | CDR3 |
| A8 | GFTFDDYA (SEQ ID NO: 1) | ISWNSGNI (SEQ ID NO: 2) | CAKDISYGSGSSFDY (SEQ ID NO: 3) | SSDVGGYNY (SEQ ID NO: 4) | GVT (SEQ ID NO: 5) | LSYAGSYNWV (SEQ ID NO: 6) |
| A11 | GFTFSSYG (SEQ ID NO: 7) | ISYDGSNK (SEQ ID NO: 8) | CAKVTSGGDFWS GNYYYYMDV (SEQ ID NO: 9) | SLRDYY (SEQ ID NO: 10) | GKN (SEQ ID NO: 11) | NSRGSSGNQWV (SEQ ID NO: 12) |
| B9 | GGTFSSYA (SEQ ID NO: 13) | IIPIFGTA (SEQ ID NO: 14) | CARPMDRYSLTT PLAFDI (SEQ ID NO: 15) | SSDVGGYDY (SEQ ID NO: 16) | EVS (SEQ ID NO: 17) | SSYAGSNDLV (SEQ ID NO: 18) |
| D12 | GYTFTGYY (SEQ ID NO: 19) | INPNSGGT (SEQ ID NO: 20) | CAKDQWLGHYGMDV (SEQ ID NO: 21) | QGISSS (SEQ ID NO: 22) | AAS (SEQ ID NO: 23) | QQTYHTPQT (SEQ ID NO: 24) |

The term "antibody" as used herein refers to a protein molecule which includes an immunoglobulin molecule having immunological reactivity with a specific antigen and plays a role as a receptor that specifically recognizes an antigen. For example, the antibody may all include a monoclonal antibody, a polyclonal antibody, a full-length antibody, and an antibody fragment. In addition, the term "antibody" as used herein may include a bivalent or bispecific molecule (e.g., a bispecific antibody), a diabody, a triabody, or a tetrabody.

The term "monoclonal antibody" as used herein refers to an antibody molecule of a single molecular composition obtained from a group of substantially identical antibodies, and such monoclonal antibody exhibits single avidity and affinity for a specific epitope, unlike a polyclonal antibody capable of binding to multiple epitopes. The term "full-length antibody" as used herein has a structure with two full-length light chains and two full-length heavy chains, wherein each light chain is connected to the heavy chain by a disulfide bond. The heavy chain constant region has gamma (γ), mu (μ), alpha (α), delta (δ), and epsilon (ε) types with subclasses including gamma 1 (γ1), gamma 2 (γ2), gamma 3 (γ3), gamma 4 (γ4), alpha 1 (α1), and alpha 2 (α2). The constant region of the light chain has kappa (κ) and lambda 00 types. IgG is a subtype, including IgG1, IgG2, IgG3, and IgG4.

The term "heavy chain" as used herein may include both a full-length heavy chain and fragment thereof, including a variable region VH including an amino acid sequence having a variable region sequence sufficient to give specificity to an antigen and three constant regions including CH1, CH2, and CH3. In addition, the term "light chain" as used herein may include both a full-length light chain and fragment thereof, including a variable region VL including an amino acid sequence having a variable region sequence sufficient to give specificity to an antigen and a constant region CL.

In an example embodiment of the present disclosure, the terms "fragment", "antibody fragment", and "antigen-binding fragment" are used interchangeably to refer to any fragment of the antibody of an example embodiment of the present disclosure, exhibiting an antigen-binding function of the antibody. Exemplary antigen-binding fragments include Fab, Fab', F(ab')2, and Fv, but are not limited thereto.

The antibody or antigen-binding fragment thereof of an example embodiment of the present disclosure may include not only the sequence of the antibody described herein, but also a biological equivalent thereof within a range that the ability to specifically bind to GFRAL is exhibited. For example, additional modifications may be applied to the amino acid sequence of an antibody to further improve binding affinity and/or other biological properties of the antibody. Such modifications include, for example, deletions, insertions, and/or substitutions of amino acid sequence residues of the antibody. Such amino acid variations are made based on the relative similarity of amino acid side chain substituents, such as hydrophobicity, hydrophilicity, charge, and size. According to analysis for the size, shape, and type of the amino acid side chain substituents, it is found that arginine, lysine, and histidine are all positively charged residues; alanine, glycine, and serine have similar sizes; and phenylalanine, tryptophan, and tyrosine have similar shapes. Therefore, based on this, arginine, lysine, and histidine; alanine, glycine, and serine; and phenylalanine, tryptophan, and tyrosine may be considered to be biologically functional equivalents.

In addition, an example embodiment of the present disclosure provides a nucleic acid molecule encoding the anti-GFRAL antibody or antigen-binding fragment thereof.

The term "nucleic acid molecule" as used herein may comprehensively include DNA (gDNA and cDNA) and RNA molecules, and nucleotides, a basic structural unit of nucleic acid molecules, include natural nucleotides as well as analogs in which sugar or base sites are modified. The sequences of the nucleic acid molecules encoding the heavy and light chain variable regions of an example embodiment of the present disclosure may be modified, and the modification includes additions, deletions, or non-conservative or conservative substitutions of nucleotides.

In addition, an example embodiment of the present disclosure provides a recombinant expression vector including the nucleic acid molecule.

In an example embodiment of the present disclosure, the term "vector" as used herein refers to a self-replicating DNA molecule used to carry a clonal gene (or another piece of clonal DNA).

In an example embodiment of the present disclosure, the term "expression vector" as used herein refers to a recombinant DNA molecule including a desired coding sequence and an appropriate nucleic acid sequence essential for expressing a coding sequence operably linked in a specific host organism. The expression vector may preferably include one or more selectable markers. The marker refers to a nucleic acid sequence having characteristics selectable by a conventional chemical method, including all genes capable of distinguishing transformed cells from non-transformed cells. Examples include antibiotic resistance genes such as ampicillin, kanamycin, geneticin (G418), bleomycin, hygromycin, and chloramphenicol but are limited thereto, and may be appropriately selected by those skilled in the art.

To express the DNA sequences of an example embodiment of the present disclosure, any one of a wide variety of expression regulatory sequences may be used in the vector. Examples of useful expression regulatory sequences may include, for example, early and late promoters of SV40 or adenovirus, promoters and enhancers of CMV, LTR of retrovirus, lac system, trp system, TAC or TRC system, T3 and T7 promoters, major operator and promoter regions of phage lambda, regulatory regions of fd code protein, promoters for 3-phosphoglycerate kinase or other glycolytic enzymes, promoters of the phosphatases such as Pho5, promotors of yeast alpha-crossing system and other sequences of composition and induction known to regulate expression of genes in prokaryotic or eukaryotic cells or viruses thereof, and various combinations thereof.

For the vector expressing the antibody of an example embodiment of the present disclosure, a vector system in which a light chain and a heavy chain are expressed simultaneously in a single vector or a system in which a light chain and a heavy chain are expressed in separate vectors respectively may all be possible. In the latter case, both vectors are introduced into host cells through co-transformation and targeted transformation. Co-transformation is a method of selecting cells expressing both the light and heavy chains after simultaneously introducing each vector DNA encoding the light and heavy chains into a host cell. Targeted transformation is a method of selecting cells transformed with a vector including a light chain (or a heavy chain) and re-transforming the selected cells expressing the light chain with a vector including a heavy chain (or a light chain) to finally select cells expressing both the light chain and the heavy chain.

In addition, an example embodiment of the present disclosure provides a cell transformed with the recombinant expression vector.

Cells capable of stably and continuously cloning and expressing the vector of an example embodiment of the present disclosure may be any host cell known in the art, including, for example, prokaryotic host cells such as *Escherichia coli, Bacillus* sp. strains such as *Bacillus subtilis* and *Bacillus thuringiensis, Streptomyces, Pseudomonas* (e.g., *Pseudomonas putida*), *Proteus mirabilis* or *Staphylococcus* (e.g., *Staphylococcus carnosus*), but are not limited thereto.

In the method for preparing the antibody or antigen-binding fragment thereof, the transformed cell may be cultured according to an appropriate medium and culture conditions known in the art. Such a culture process may be easily adjusted to be used by those skilled in the art depending on the selected strain. Cell culture is divided into suspension culture and adherent culture depending on the cell growth type, and batch, fed-batch, and continuous culture methods depending on the culture type. The medium used for culture should suitably satisfy the requirements for a particular strain.

In addition, an example embodiment of the present disclosure provides a pharmaceutical composition for preventing or treating cancer-related anorexia-cachexia syndrome (CACS), including the anti-GFRAL antibody or antigen-binding fragment thereof as an active ingredient.

The pharmaceutical composition of an example embodiment of the present disclosure may further include a pharmaceutically acceptable carrier, and the pharmaceutically acceptable carrier is commonly used in the formulation, including lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, and mineral oil, but is not limited thereto. The composition of an example embodiment of the present disclosure may further include a lubricant, a wetting agent, a sweetener, a flavoring agent, an emulsifier, a suspending agent, and a preservative, in addition to the above components.

The pharmaceutical composition of an example embodiment of the present disclosure may be administered orally or parenterally, and in the case of parenteral administration, administration may be performed by intravenous injection, subcutaneous injection, intramuscular injection, intraperitoneal injection, endothelial administration, topical administration, intranasal administration, intrapulmonary administration, and rectal administration. When administered orally, the composition for oral administration may be formulated by coating an active agent or protecting the same from degradation in the stomach since protein or peptide is digested, and the composition of an example embodiment of the present disclosure may be administered by any device that allows the active ingredient to be delivered to a target cell.

A suitable dose of the pharmaceutical composition of an example embodiment of the present disclosure varies depending on factors such as formulation method, administration type, age, weight, sex, pathological condition, food, administration time, administration route, excretion rate, and response sensitivity of a patient, and a generally skilled physician may easily determine and prescribe an effective dose for the desired treatment or prevention.

The pharmaceutical composition of an example embodiment of the present disclosure may be formulated in a unit dosage form by using a pharmaceutically acceptable carrier and/or excipient or prepared by being introduced into a multi-dose container according to a method that may be easily carried out by a person of ordinary skill in the art to which the present disclosure pertains. In this case, the formulation may be in the form of a solution, suspension, or emulsion in oil or aqueous medium, or may be in the form of an extract, powder, suppository, powder, granule, tablet, or capsule, and may additionally include a dispersing agent or a stabilizer.

In addition, an example embodiment of the present disclosure provides a health functional food composition for preventing or alleviating cancer-related anorexia-cachexia syndrome (CACS), including the anti-GFRAL antibody or antigen-binding fragment thereof as an active ingredient.

The health functional food composition may be provided in the form of powder, granules, tablets, capsules, syrups, beverages, or pills. The health food composition is used together with other food or food additives in addition to the composition according to an example embodiment of the present disclosure as an active ingredient, and may be appropriately applied according to the conventional method. The mixed amount of the active ingredient may be suitably determined depending on the purpose of use thereof such as prophylactic, health, or therapeutic treatment.

The effective dose of the antibody or antigen-binding fragment thereof included in the health functional food composition may be used according to the effective dose of the pharmaceutical composition, but for the long-term intake for a purpose of health and hygiene or health control, the dose may be less than the above range. In addition, since there is no problem in terms of safety, it is certain that the dose may be beyond the above range.

The type of health food is not particularly limited, and examples may include meat, sausage, bread, chocolate, candy, snacks, confectionery, pizza, ramen, other noodles, gum, dairy products such as ice cream, various soups, beverages, tea, drinks, alcoholic beverages, and vitamin complexes.

In addition, an example embodiment of the present disclosure provides a pharmaceutical composition for preventing or treating anorexia or cachexia caused by an anticancer agent, including the anti-GFRAL antibody or antigen-binding fragment thereof as an active ingredient.

In addition, an example embodiment of the present disclosure provides a health functional food composition for preventing or alleviating anorexia or cachexia caused by an anticancer agent, including the anti-GFRAL antibody or antigen-binding fragment thereof as an active ingredient.

More preferably, the anticancer agent may be one or more selected from the group consisting of cisplatin, oxaliplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristine, vinblastine, and methotrexate, but is not limited thereto.

In addition, the anti-GFRAL antibody or antigen-binding fragment thereof of an example embodiment of the present disclosure may be used as an anticancer adjuvant. In an example embodiment of the present disclosure, the anticancer adjuvant may refer to alleviation of side effects caused when administrating the anticancer agent. That is, by administering the anticancer adjuvant of an example embodiment of the present disclosure in combination with an anticancer agent, it is possible to prevent the occurrence of various side effects caused by the anticancer agent. The adjuvant of an example embodiment of the present disclosure may be administered simultaneously, separately, or sequentially with the anticancer agent. The administration order of the anti-cancer adjuvant according to an example embodiment of the present disclosure, that is, which one of the anti-cancer agent and the anti-cancer adjuvant is to be simultaneously, individually or sequentially administered at which point of time may be determined by a physician or an expert. The administration order may vary depending on many factors.

MODES FOR CARRYING OUT INVENTION

Hereinafter, examples will be described in detail to help the understanding of the present disclosure. However, the following examples are merely illustrative of the content of the present disclosure, and the scope of the present disclosure is not limited to the following examples. The example embodiments of the present disclosure are provided to more completely explain the present disclosure to those of ordinary skill in the art.

<Example 1> Cell Culture

HEK-293FT cells (human embryonic kidney) were cultured in DMEM medium (Hyclone) supplemented with 10% fetal bovine serum, 1% penicillin, and streptomycin, and Expi-293F cells (human embryonic kidney) were cultured in Expi-293 expression medium (Gibco).

<Example 2> Phage Display Method

Phage display using a human patient-derived scFv library was conducted after attaching recombinant human GFRAL (#9647-GR, R&D systems) or recombinant mouse GFRAL (#9844-GR, R&D systems) to Dynabeads M-270 epoxy beads (#14301, Invitrogen). Panning was performed twice for each of the human GFRAL and the mouse GFRAL, alternatively. After phage was subjected to a reaction with general beads at room temperature for 1 hour, an unbound supernatant was reacted with GFRAL-bound beads for 2 hours. After washing 3-8 times, the phage bound to GFRAL was eluted using recombinant human GDF15 ligand (#8146-GD, R&D systems) or an acidic buffer (0.1 M glycine-hydrogen chloride, pH 2.2).

<Example 3> Polyclonal Phage Enzyme-Linked Immunosorbent Assay

A 96-well half area plate (#3690, Corning) was coated by reacting the same with recombinant human GFRAL, recombinant mouse GFRAL, or bovine serum albumin overnight at 4° C., and then washed once with PBS. Then, blocking was performed at 37° C. for 1 hour with PBS in which 5% skim milk is contained. After a reaction with a phage library for each round at 37° C. for 2 hours, washing was followed 5 times using PBS, a reaction was carried out with HRP-conjugated anti-phage antibody (#11973-MM05T-H, Sino Biological) at 37° C. for 1 hour, and washing was performed 5 times with PBS. Finally, color development was performed using TMB at room temperature for 10 minutes, which was then stopped using a stop solution. Thereafter, absorbance was measured at a wavelength of 450 nm using a microplate reader.

<Example 4> Monoclonal Phage Enzyme-Linked Immunosorbent Assay

To harvest monoclonal phage, SB media, in which carbenicillin (#C1389, Sigma) is contained at a concentration of 50 ug/ml in each well of a 96 well deep well plate (#90060, Bioneer), was dispensed, and colonies including the phage library were inoculated, followed by culture at 37° C. and 250 rpm for 3 hours. Then, the M13K07 helper phage was treated at a concentration of $10^{10}$ phage/ml, and additional culture was followed under the same condition for 2 hours. Thereafter, kanamycin (#K4000, Sigma) was treated at a concentration of 70 ug/ml and culture was performed overnight. In the process of the phage enzyme-linked immunosorbent assay, a portion of the culture medium was treated after blocking, and the rest of the process was performed in the same manner as in the polyclonal phage enzyme-linked immunosorbent assay.

<Example 5> Purification Method Using High Performance Liquid Chromatography

The scFv sequence of a monoclone having binding ability to GFRAL was transferred to an expression vector constructed based on pFUSE vector (#pfuse hg1fc2, InvivoGen) using sfiI restriction enzyme, and then transfected into Expi293F cells. Transfection was performed using Expi-Fectamine 293 Transfection Kit (#A14524, Gibco). Expi293F cells were cultured in a 500 ml flask at a density of about $2.5 \times 10^6$ cells/ml and treated with a mixture obtained by mixing ExpiFectamine 293 Reagent and scFv-expressing vector in Opti-MEM (#31985-070, Gibco) medium, followed by overnight culture at 37° C. and 125 rpm. The next day, after treatment of ExpiFectamine 293 Transfection Enhancer 1 and 2, culture was additionally conducted for 3 days to generate antibody in a form of scfv-Fc. Thereafter, the supernatant was purified using AKTA prime plus (GE healthcare) purifier and IgG separation column (#17-0404-01, GE healthcare). After attaching the antibody to the column using 20 mM sodium phosphate buffer (pH 7.4), elution was followed using 0.1 M glycine-hydrogen chloride buffer (pH 2.7). Then, concentration was performed using Amicon Ultra-4-30K (#UFC803024, Millipore), followed by sterilization with a Spin-X filter (#8160, Corning). Endotoxin was removed using an endotoxin removal column (#88274, Thermo Fisher Scientific), and the concentration was measured using a BCA kit (#23227, Thermo Fisher Scientific).

<Example 6> Antibody Enzyme-Linked Immunosorbent Assay

A 96-well half area plate was coated by reacting the same with recombinant human GFRAL, recombinant mouse GFRAL, or bovine serum albumin overnight at 4° C. Using clonal scFv-Fc antibody as the primary antibody and HRP-conjugated anti-human IgG antibody as the secondary antibody (#Ab97225, Abcam), enzyme-linked immunosorbent assay was performed.

<Example 7> Transfection into HEK-293FT Cells

HEK-293FT cells were inoculated into 6-well plates at a density of about $1 \times 10^6$ cells/well and treated with a mixture obtained by mixing Lipofectamine 2000 Reagent (#11668-027, Thermo Fisher Scientific), a GFRAL-expressing vector (#OHu31183D, GenScript), and RET-expressing vector (#HG11997-CF, Sino Biological) in Opti-MEM medium at a ratio of 1:1, followed by overnight culture at 37° C. The next day, the supernatant was removed, and the medium was replaced with a fresh medium supplemented with 10% fetal bovine serum. After injecting a vector enabling expression of luciferase in the ERK signal transduction process, overnight culture was followed at 37° C., and a supernatant was removed the next day. A process of replacing the medium with a fresh medium supplemented with 10% fetal bovine serum was further conducted.

<Example 8> Immunocytochemistry

The transfected HEK-293FT cells were inoculated into a 4-well cell culture slide (#154526, Thermo Fisher Scientific) at a density of about $5 \times 10^4$ cells/well, and immobilization was performed by treating 4% paraformaldehyde at room temperature for 10 minutes. After that, blocking was performed for 1 hour using 0.1% PBST (Tween 20) containing 1% BSA and 5% goat serum. After that, a reaction was followed with clonal antibody purified with primary antibody or commercial GFRAL antibody (#Ab107719, Abcam) for 1 hour. After washing 3-5 times with PBST, a reaction was performed with FITC-conjugated anti-human IgG antibody (#97224, Abcam) or anti-rabbit IgG antibody (#A11008, Invitrogen) for 1 hour. After washing 3-5 times with PBST, DAPI-containing PBS was treated for 15 minutes. After mounting, fluorescence was observed under a microscope.

<Example 9> Surface Plasmon Resonance Analysis

A Biacore SPR system was applied to measure the degree of binding of the clonal antibody to human recombinant GFRAL. As a ligand, human recombinant GFRAL was dissolved in 20 mM sodium acetate, and then immobilized onto a PEG chip via an amine bond at pH 6.0. Thereafter, the binding assay was performed using, as an analyte, a clonal antibody dissolved in PBS at pH 7.4, and injection was followed at a flow rate of 30 µl/ml. The time allotted for association and dissociation was 4 minutes and 6 minutes, respectively. The surface of a sensor was regenerated by injecting 5-10 mM sodium hydroxide. The association curve as well as values for association constant $K_a$, dissociation constant $K_d$, and equilibrium constant $K_D$ were calculated using Scrubber2 (Biologic Software) software.

As a result of the experiment, the binding curve was derived as shown in FIG. 9. The value of association constant $K_a$ was $5.556 \times 10^{-5}$/M·s, and that of dissociation constant $K_d$ was $1.083 \times 10^{-3}$/s. The value of equilibrium constant $K_D$ was 1.95 nM, calculated by a formula represented by $K_D = K_d/K_a$.

<Example 10> Analysis of Luciferase Expression by Antibody

The transfected HEK-293FT cells were inoculated into a 96-well plate at a density of about $7 \times 10^4$ cells/well, maintained under a serum-deficient condition for 2 hours, and then subjected to a reaction by treatment of clonal antibody for 2 hours. After that, human recombinant GDF15 was treated for 5 minutes, and the degree of luminescence was measured using a reagent (#E2610, Promega) containing a substrate of luciferase enzyme.

As a result of the experiment as shown in FIG. 10, it was found that the luminescence value increased when only GDF15 was treated and decreased in a concentration dependent manner in the experimental group pretreated with clone A11 and D12.

<Example 11> Analysis of pERK Expression by Antibody

The transfected HEK-293FT cells were inoculated into a 24-well plate at a density of about $2 \times 10^5$ cells/well, maintained under a serum-deficient condition for 2 hours, and then subjected to a reaction by treatment of clonal antibody for 2 hours. Thereafter, human recombinant GDF15 was treated for 5 minutes, washing was performed with PBS, and cells were harvested to perform Western blot. Cytoplasmic or cell membrane proteins were isolated by SDS-PAGE and transferred to a nitrocellulose membrane. Then, culture was performed with primary antibody, and then with the HRP-conjugated secondary antibody, respectively. Images were visualized using ECL detection reagent (#34095, Thermo Fisher Scientific, #RPN2209, GE Healthcare) and quantified using ECL hyperfilm (AGFA, Morstel) Images in the film were quantified using ImageJ program and graphed using IC50 calculator of AAT Bioquest.

As a result of the experiment as shown in FIG. 11, it was found that the expression level of pERK increased in the experimental group treated with only GDF15 and that of pERK decreased in a concentration dependent manner in the experimental group pretreated with clone A11. The measured IC50 value was 4.9 µg/ml. The images in the film were quantified and shown in FIG. 12.

<Example 12> Analysis of Side Effect Alleviation of Cisplatin by Antibody Cisplatin was injected at a concentration of 10 mg/kg into 8-week-old mice, and 10 mg/kg of ineffective control antibody or clone A11 was injected so as to check whether the cisplatin-induced side effects were alleviated. The drug was injected twice a week.

As a result of the experiment, it was found that the weight reduction effect induced by cisplatin was recovered by A11 as shown in FIG. 13, and the appetite reduction effect was also alleviated as shown in FIG. 14. As shown in FIG. 15, no difference was found in the expression level of GDF15 between the control group and the A11-treated group. The specific changes in the weight of fat and muscle were quantified and shown in FIGS. 16 and 17. As shown in FIG. 18, it was found that the effect of A11 was derived through inhibition of an action of GFRAL in the mouse brain.

<Example 13> Immunohistochemistry

Brain tissue, obtained by fixating the mice in the experiment in Example 12 by perfusion fixation, was frozen sectioned to a thickness of 30 µm. The sectioned tissue was blocked using 0.1% PBST (Tween 20) containing 1% BSA and 5% goat serum for 1 hour, and then a reaction was carried out for 1 hour using a commercial GFRAL antibody (#Ab107719, Abcam) and c-Fos antibody (#sc-166940, Santa cruz biotechnology) as primary antibody. After washing with PBST 5 times, a reaction was carried out, for 1 hour, with Alexa fluor 488-conjugated anti-mouse IgG antibody (#A11001, Invitrogen) and Alexa fluor 594-conjugated anti-rabbit IgG antibody (#A11008, Invitrogen). After washing with PBST 5 times, DAPI-containing PBS was treated for 15 minutes. After mounting, fluorescence was observed under a microscope.

<Example 14> Analysis of Side Effect Alleviation of Cisplatin by Antibody in an Allograft Mouse Tumor Model B16F10-Luc cells, counted by $1 \times 10^6$ approximately, were injected into 8-week-old mice. After the tumor grew to a certain size or bigger, cisplatin was injected at a concentration of 10 mg/kg, and an ineffective control antibody or clone A11 was injected by 10 mg/kg so as to check whether the side effects induced by cisplatin were alleviated in the chemotherapy model. The drug was injected twice a week.

As a result of the experiment, it was found that the weight reduction effect induced by cisplatin was recovered by A11 under condition involved with chemotherapy as shown in FIG. 19. In addition, it was also found that the appetite reduction effect was alleviated as shown in FIG. 20. As shown in FIG. 21, no difference was found in the expression level of GDF15 between the control group and the A11-treated group. The specific changes in the weight of fat and muscle are quantified and shown in FIGS. 22 and 23.

Although specific parts of the present disclosure have been described in detail above, it is clear for those skilled in the art that these specific techniques are merely preferred example embodiments and the scope of the present disclosure is not limited thereto. Accordingly, the substantial scope of the present disclosure will be defined by the appended claims and equivalents thereof.

What is claimed is:

1. An anti-GFRAL antibody or antigen-binding fragment thereof, comprising a heavy chain variable region comprising a heavy chain CDR1 comprising an amino acid sequence represented by SEQ ID NO: 7, a heavy chain CDR2 comprising an amino acid sequence represented by SEQ ID NO: 8, and a heavy chain CDR3 comprising an amino acid sequence represented by SEQ ID NO: 9; and a light chain variable region comprising a light chain CDR1 comprising an amino acid sequence represented by SEQ ID NO: 10, a light chain CDR2 comprising an amino acid sequence represented by SEQ ID NO: 11, and a light chain CDR3 comprising an amino acid sequence represented by SEQ ID NO: 12.

2. A method of treating cancer-related anorexia-cachexia syndrome (CACS), the method comprising administering to a patient in need thereof an effective amount of the anti-GFRAL antibody according to claim 1 or an antigen-binding fragment thereof as an active ingredient.

3. A method of treating anorexia or cachexia caused by an anticancer agent, the method comprising administering to a patient in need thereof an effective amount of the anti-GFRAL antibody according to claim 1 or an antigen-binding fragment thereof as an active ingredient.

4. The method of claim 3, wherein the anticancer agent is one or more selected from the group consisting of cisplatin, oxaliplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristine, vinblastine, and methotrexate.

* * * * *

SEQUENCE LISTING

<160> NUMBER OF SEQ ID NOS: 24

<210> SEQ ID NO 1
<211> LENGTH: 8
<212> TYPE: PRT
<213> ORGANISM: Artificial Sequence
<220> FEATURE:
<223> OTHER INFORMATION: A8 VH CDR1

<400> SEQUENCE: 1

Gly Phe Thr Phe Asp Asp Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: A8 VH CDR2

<400> SEQUENCE: 2

Ile Ser Trp Asn Ser Gly Asn Ile
1               5

<210> SEQ ID NO 3
<211> LENGTH: 15
<212> TYPE: PRT
<213> ORGANISM: Artificial Sequence
<220> FEATURE:
<223> OTHER INFORMATION: A8 VH CDR3

<400> SEQUENCE: 3

Cys Ala Lys Asp Ile Ser Tyr Gly Ser Gly Ser Ser Phe Asp Tyr
1               5                   10                  15

<210> SEQ ID NO 4
<211> LENGTH: 9
<212> TYPE: PRT
<213> ORGANISM: Artificial Sequence
<220> FEATURE:
<223> OTHER INFORMATION: A8 VL CDR1

<400> SEQUENCE: 4

Ser Ser Asp Val Gly Gly Tyr Asn Tyr
1               5

<210> SEQ ID NO 5
<211> LENGTH: 3
<212> TYPE: PRT
<213> ORGANISM: Artificial Sequence
<220> FEATURE:
<223> OTHER INFORMATION: A8 VL CDR2

<400> SEQUENCE: 5

Gly Val Thr
1

<210> SEQ ID NO 6
<211> LENGTH: 10
<212> TYPE: PRT
<213> ORGANISM: Artificial Sequence
<220> FEATURE:
<223> OTHER INFORMATION: A8 VL CDR3

<400> SEQUENCE: 6

Leu Ser Tyr Ala Gly Ser Tyr Asn Trp Val
1               5                   10

```
<210> SEQ ID NO 7
<211> LENGTH: 8
<212> TYPE: PRT
<213> ORGANISM: Artificial Sequence
<220> FEATURE:
<223> OTHER INFORMATION: A11 VH CDR1

<400> SEQUENCE: 7

Gly Phe Thr Phe Ser Ser Tyr Gly
1               5

<210> SEQ ID NO 8
<211> LENGTH: 8
<212> TYPE: PRT
<213> ORGANISM: Artificial Sequence
<220> FEATURE:
<223> OTHER INFORMATION: A11 VH CDR2

<400> SEQUENCE: 8

Ile Ser Tyr Asp Gly Ser Asn Lys
1               5

<210> SEQ ID NO 9
<211> LENGTH: 21
<212> TYPE: PRT
<213> ORGANISM: Artificial Sequence
<220> FEATURE:
<223> OTHER INFORMATION: A11 VH CDR3

<400> SEQUENCE: 9

Cys Ala Lys Val Thr Ser Gly Gly Asp Phe Trp Ser Gly Asn Tyr Tyr
1               5                   10                  15

Tyr Tyr Met Asp Val
            20

<210> SEQ ID NO 10
<211> LENGTH: 6
<212> TYPE: PRT
<213> ORGANISM: Artificial Sequence
<220> FEATURE:
<223> OTHER INFORMATION: A11 VL CDR1

<400> SEQUENCE: 10

Ser Leu Arg Asp Tyr Tyr
1               5

<210> SEQ ID NO 11
<211> LENGTH: 3
<212> TYPE: PRT
<213> ORGANISM: Artificial Sequence
<220> FEATURE:
<223> OTHER INFORMATION: A11 VL CDR2

<400> SEQUENCE: 11

Gly Lys Asn
1

<210> SEQ ID NO 12
<211> LENGTH: 11
<212> TYPE: PRT
<213> ORGANISM: Artificial Sequence
<220> FEATURE:
<223> OTHER INFORMATION: A11 VL CDR3

<400> SEQUENCE: 12
```

```
Asn Ser Arg Gly Ser Ser Gly Asn Gln Trp Val
1               5                   10

<210> SEQ ID NO 13
<211> LENGTH: 8
<212> TYPE: PRT
<213> ORGANISM: Artificial Sequence
<220> FEATURE:
<223> OTHER INFORMATION: B9 VH CDR1

<400> SEQUENCE: 13

Gly Gly Thr Phe Ser Ser Tyr Ala
1               5

<210> SEQ ID NO 14
<211> LENGTH: 8
<212> TYPE: PRT
<213> ORGANISM: Artificial Sequence
<220> FEATURE:
<223> OTHER INFORMATION: B9 VH CDR2

<400> SEQUENCE: 14

Ile Ile Pro Ile Phe Gly Thr Ala
1               5

<210> SEQ ID NO 15
<211> LENGTH: 18
<212> TYPE: PRT
<213> ORGANISM: Artificial Sequence
<220> FEATURE:
<223> OTHER INFORMATION: B9 VH CDR3

<400> SEQUENCE: 15

Cys Ala Arg Pro Met Asp Arg Tyr Ser Leu Thr Thr Pro Leu Ala Phe
1               5                   10                  15

Asp Ile

<210> SEQ ID NO 16
<211> LENGTH: 9
<212> TYPE: PRT
<213> ORGANISM: Artificial Sequence
<220> FEATURE:
<223> OTHER INFORMATION: B9 VL CDR1

<400> SEQUENCE: 16

Ser Ser Asp Val Gly Gly Tyr Asp Tyr
1               5

<210> SEQ ID NO 17
<211> LENGTH: 3
<212> TYPE: PRT
<213> ORGANISM: Artificial Sequence
<220> FEATURE:
<223> OTHER INFORMATION: B9 VL CDR2

<400> SEQUENCE: 17

Glu Val Ser
1

<210> SEQ ID NO 18
<211> LENGTH: 10
<212> TYPE: PRT
<213> ORGANISM: Artificial Sequence
<220> FEATURE:
<223> OTHER INFORMATION: B9 VL CDR3

<400> SEQUENCE: 18
```

Ser Ser Tyr Ala Gly Ser Asn Asp Leu Val
1               5                   10

<210> SEQ ID NO 19
<211> LENGTH: 8
<212> TYPE: PRT
<213> ORGANISM: Artificial Sequence
<220> FEATURE:
<223> OTHER INFORMATION: D12 VH CDR1

<400> SEQUENCE: 19

Gly Tyr Thr Phe Thr Gly Tyr Tyr
1               5

<210> SEQ ID NO 20
<211> LENGTH: 8
<212> TYPE: PRT
<213> ORGANISM: Artificial Sequence
<220> FEATURE:
<223> OTHER INFORMATION: D12 VH CDR2

<400> SEQUENCE: 20

Ile Asn Pro Asn Ser Gly Gly Thr
1               5

<210> SEQ ID NO 21
<211> LENGTH: 14
<212> TYPE: PRT
<213> ORGANISM: Artificial Sequence
<220> FEATURE:
<223> OTHER INFORMATION: D12 VH CDR3

<400> SEQUENCE: 21

Cys Ala Lys Asp Gln Trp Leu Gly His Tyr Gly Met Asp Val
1               5                   10

<210> SEQ ID NO 22
<211> LENGTH: 6
<212> TYPE: PRT
<213> ORGANISM: Artificial Sequence
<220> FEATURE:
<223> OTHER INFORMATION: D12 VL CDR1

<400> SEQUENCE: 22

Gln Gly Ile Ser Ser Ser
1               5

<210> SEQ ID NO 23
<211> LENGTH: 3
<212> TYPE: PRT
<213> ORGANISM: Artificial Sequence
<220> FEATURE:
<223> OTHER INFORMATION: D12 VL CDR2

<400> SEQUENCE: 23

Ala Ala Ser
1

<210> SEQ ID NO 24
<211> LENGTH: 9
<212> TYPE: PRT
<213> ORGANISM: Artificial Sequence
<220> FEATURE:
<223> OTHER INFORMATION: D12 VL CDR3

-continued

```
<400> SEQUENCE: 24

Gln Gln Thr Tyr His Thr Pro Gln Thr
1               5
```